US010813476B2

(12) United States Patent
Kousik et al.

(10) Patent No.: US 10,813,476 B2
(45) Date of Patent: Oct. 27, 2020

(54) MEDICAL DEVICE ADAPTER BRACKET

(71) Applicant: Medline Industries, Inc., Northfield, IL (US)

(72) Inventors: Arun Kousik, Northfield, IL (US); Kyle Frye, Lindenhurst, IL (US)

(73) Assignee: MEDLINE INDUSTRIES, INC., Northfield, IL (US)

( * ) Notice: Subject to any disclaimer, the term of this patent is extended or adjusted under 35 U.S.C. 154(b) by 29 days.

(21) Appl. No.: 16/289,030

(22) Filed: Feb. 28, 2019

(65) Prior Publication Data

US 2020/0275788 A1    Sep. 3, 2020

(51) Int. Cl.
*A47F 5/08* (2006.01)
*A61B 5/00* (2006.01)
*H01R 43/00* (2006.01)
*A47B 97/00* (2006.01)
*G08B 21/02* (2006.01)

(52) U.S. Cl.
CPC .............. *A47F 5/08* (2013.01); *A61B 5/6891* (2013.01); *A61B 5/6892* (2013.01); *H01R 43/00* (2013.01); *A47B 97/001* (2013.01); *A61G 2203/34* (2013.01); *G08B 21/02* (2013.01)

(58) Field of Classification Search
CPC ......... A47F 5/08; H01R 43/00; A61B 5/6891; A61B 5/6892; A61G 2203/34; A47B 97/001; G08B 21/02
See application file for complete search history.

(56) References Cited

U.S. PATENT DOCUMENTS

| | | | | |
|---|---|---|---|---|
| 1,752,985 | A | * | 4/1930 | Huffman .................. A47F 5/13 211/106 |
| 4,678,151 | A | * | 7/1987 | Radek .................. A47F 5/0846 211/59.1 |
| 5,456,435 | A | * | 10/1995 | Sweeney ................ A47B 57/40 211/90.01 |
| 5,507,399 | A | * | 4/1996 | Hermanson ............ A47F 5/135 211/181.1 |
| 5,896,091 | A | * | 4/1999 | Soderlund ............. G08B 17/10 340/632 |
| 6,105,794 | A | * | 8/2000 | Bauer .................... A47B 57/26 108/108 |
| 6,481,678 | B1 | * | 11/2002 | Chong .................. H02G 3/288 211/192 |
| 7,417,539 | B2 | * | 8/2008 | Mathews ............... G08B 21/02 340/539.1 |
| 7,849,545 | B2 | | 12/2010 | Flocard |
| 8,537,008 | B2 | | 9/2013 | Tallent |
| 8,823,529 | B2 | | 9/2014 | Reed, Jr. |

(Continued)

*Primary Examiner* — Ko H Chan
(74) *Attorney, Agent, or Firm* — Fitch, Even, Tabin & Flannery LLP

(57) ABSTRACT

An adapter bracket securable to a wall-mounted bracket is provided. The adapter bracket generally comprises a main body portion that includes a main body panel and a second body portion having a second body panel, the second body panel being pivotally connected to the main body panel. The body panels are equipped with channels that are sized to fit a wall-mounted bracket. The pivoting second body portion allows access to the rear portion of the medical device to thereby allow access to the battery compartment. The adapter bracket can be sold as a kit with a medical device to enable the medical device to mount to a pre-existing wall-mounted bracket.

7 Claims, 19 Drawing Sheets

(56) References Cited

U.S. PATENT DOCUMENTS

| | | |
|---|---|---|
| 8,847,756 B2 | 9/2014 | Tallent |
| 8,955,680 B1 * | 2/2015 | Wu Lee .................. B65H 75/28 |
| | | 206/419 |
| 9,098,993 B2 | 8/2015 | Reed, Jr. |
| 9,541,231 B1 * | 1/2017 | Owens .................. F21V 35/003 |
| 10,559,186 B2 * | 2/2020 | Allen, Sr. ................ H04Q 9/00 |
| 2002/0017988 A1 * | 2/2002 | Irwin ..................... G01K 1/024 |
| | | 340/539.27 |
| 2018/0263119 A1 * | 9/2018 | Armiento ............... B33Y 80/00 |

* cited by examiner

-PRIOR ART-

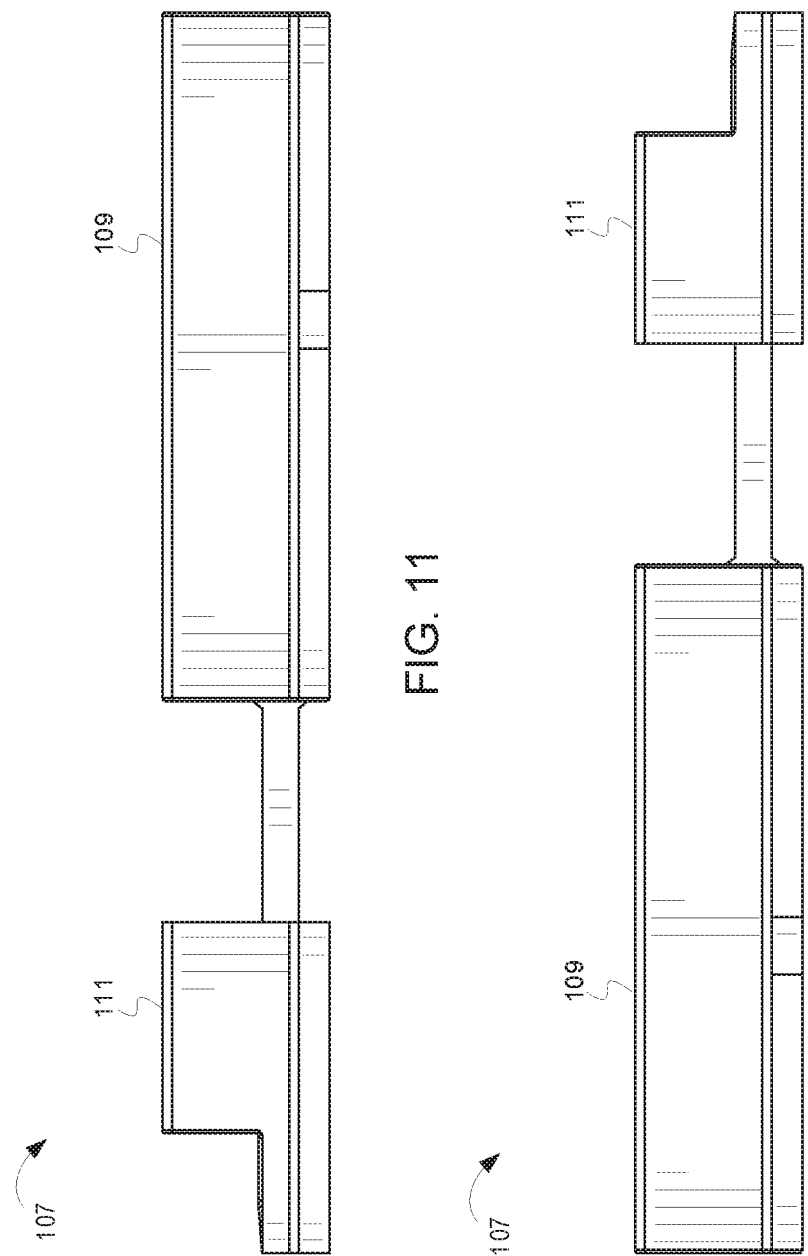

MEDICAL DEVICE ADAPTER BRACKET

TECHNICAL FIELD

This application relates generally to medical devices and, more particularly, to adapter brackets for medical devices.

BACKGROUND

Medical devices are ubiquitous in healthcare facilities, such as hospitals and clinics. A wide variety of medical devices exists that monitor varying conditions, such as heartrate, blood pressure, temperature, weight, etc. For example, devices that sense the weight of a patent are used as fall alarms. These devices generally include a pressure-sensitive mat that is placed beneath the patient, and a wall-mounted alarm that is triggered if pressure on the mat is released. The wall-mounted alarm includes a portable device that is movable from room to room as needed and a plurality of wall-mounted brackets sized to receive the device.

The brackets may be mounted in several rooms in the healthcare facility. If it is desired to replace the medical device with a device sold by a different manufacturer, new wall-mounted bracket may be required. Removal of the existing bracket may leave unsightly holes or require labor to repair the wall and mount a new bracket to support the new medical device.

It has now been found that an adapter bracket securable to a wall-mounted bracket can be provided. The adapter bracket generally comprises a main body portion that includes a main body panel and a second body portion having a second body panel, the second body panel being pivotally connected to the main body panel. The body panels are equipped with channels that are sized to fit a wall-mounted bracket. The pivoting second body portion allows access to the rear portion of the medical device to thereby allow access to the rear of the medical device, for example to access a battery compartment.

BRIEF DESCRIPTION OF THE DRAWINGS

FIGS. 11 and 12 are first and second side elevational views respectively of the adapter bracket shown in FIG. 7.

DETAILED DESCRIPTION

Figure 1:
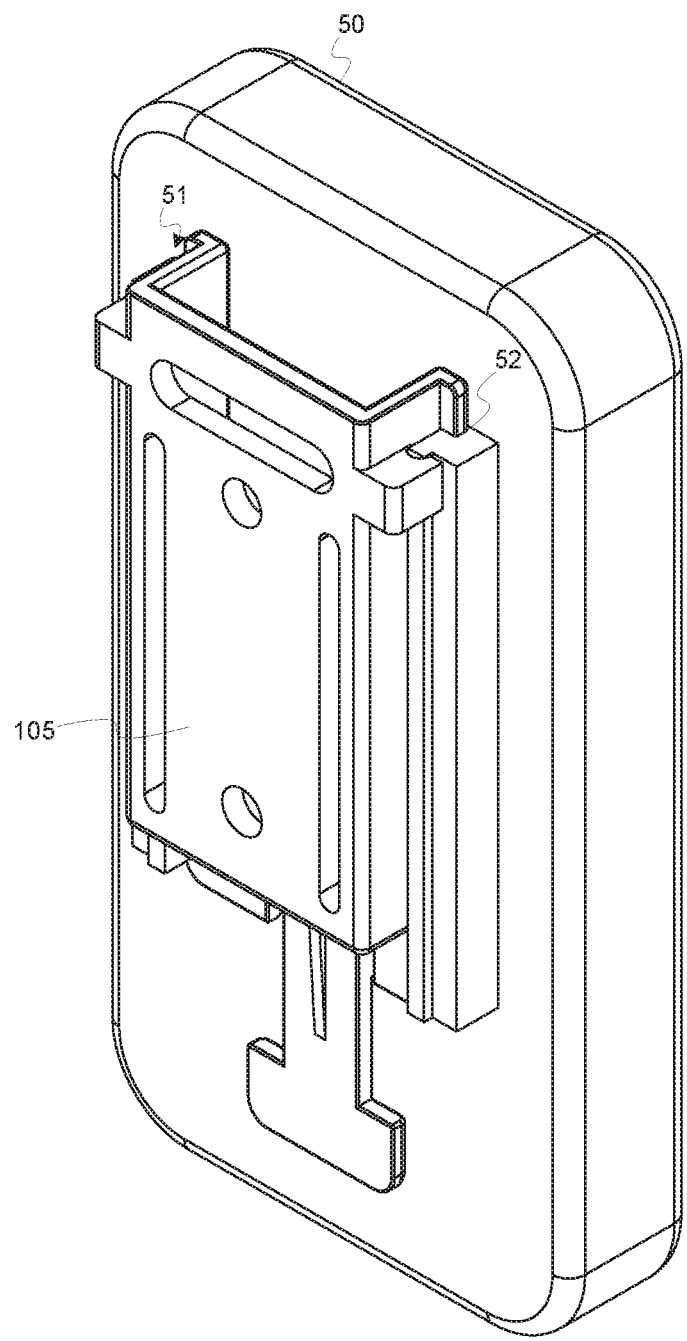
FIG. 1 is a rear perspective view of a prior art medical assembly that includes a medical device that mounts to a wall-mounted bracket.

The prior art medical device assembly shown in FIG. 1 includes a medical device 50 having rear channels 51, 52 that engage a wall-mounted bracket 105. The device 50 in the illustrated embodiment is a fall alarm. Typically, a plurality of wall-mounted brackets is secured via screws to a plurality of wall surfaces in a healthcare facility.

Figure 2:
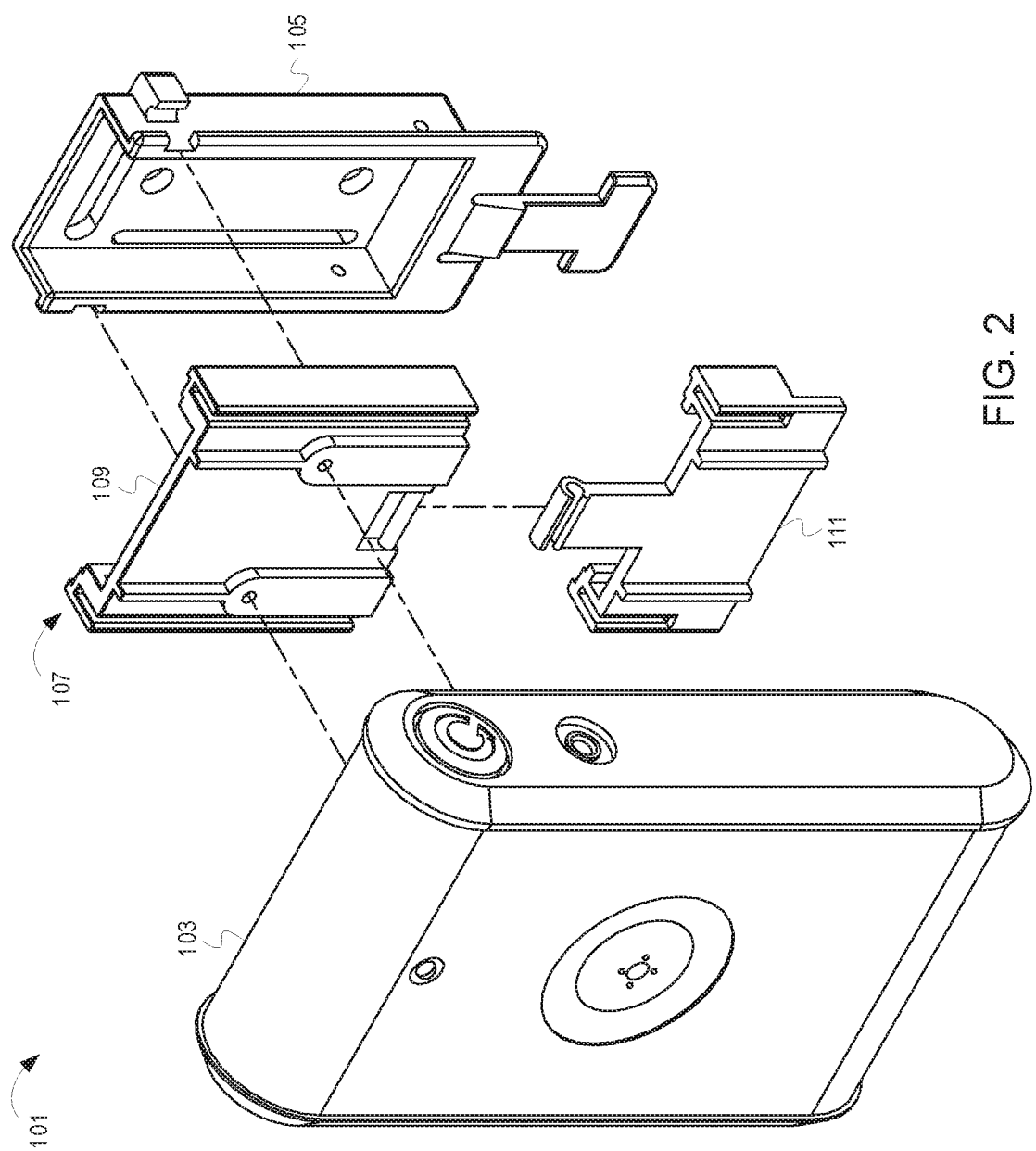
FIG. 2 is an exploded view of a medical device assembly that comprises a battery-powered medical device, the wall-mounted bracket of the prior art medical device assembly shown in FIG. 1, and an adapter bracket for securing the medical device to the wall-mounted bracket.

With reference to FIG. 2, the illustrated medical device assembly 101 comprises a medical device 103, an adapter bracket 107, and the wall-mounted bracket 105. The wall-mounted bracket 105 is configured to be secured to a wall surface and support a different medical device (i.e., a medical device that is not the medical device 103, such as the medical device 50). The different medical device can be a medical device supplied by a different manufacturer or a different type of medical device altogether.

The adapter bracket 107 is secured to the medical device 103 via screws or adhesive. Via the adapter bracket 107, the medical device 103 is securable to the wall-mounted bracket 105. In this manner, the adapter bracket 107 allows the medical device 103 to be used with the wall-mounted bracket 105 even though the wall-mounted bracket 105 was designed for use with a different medical device. As seen in FIG. 2, the adapter bracket 107 is secured to the medical device 103 and mounted on the wall-mounted bracket 105.

Figure 7:
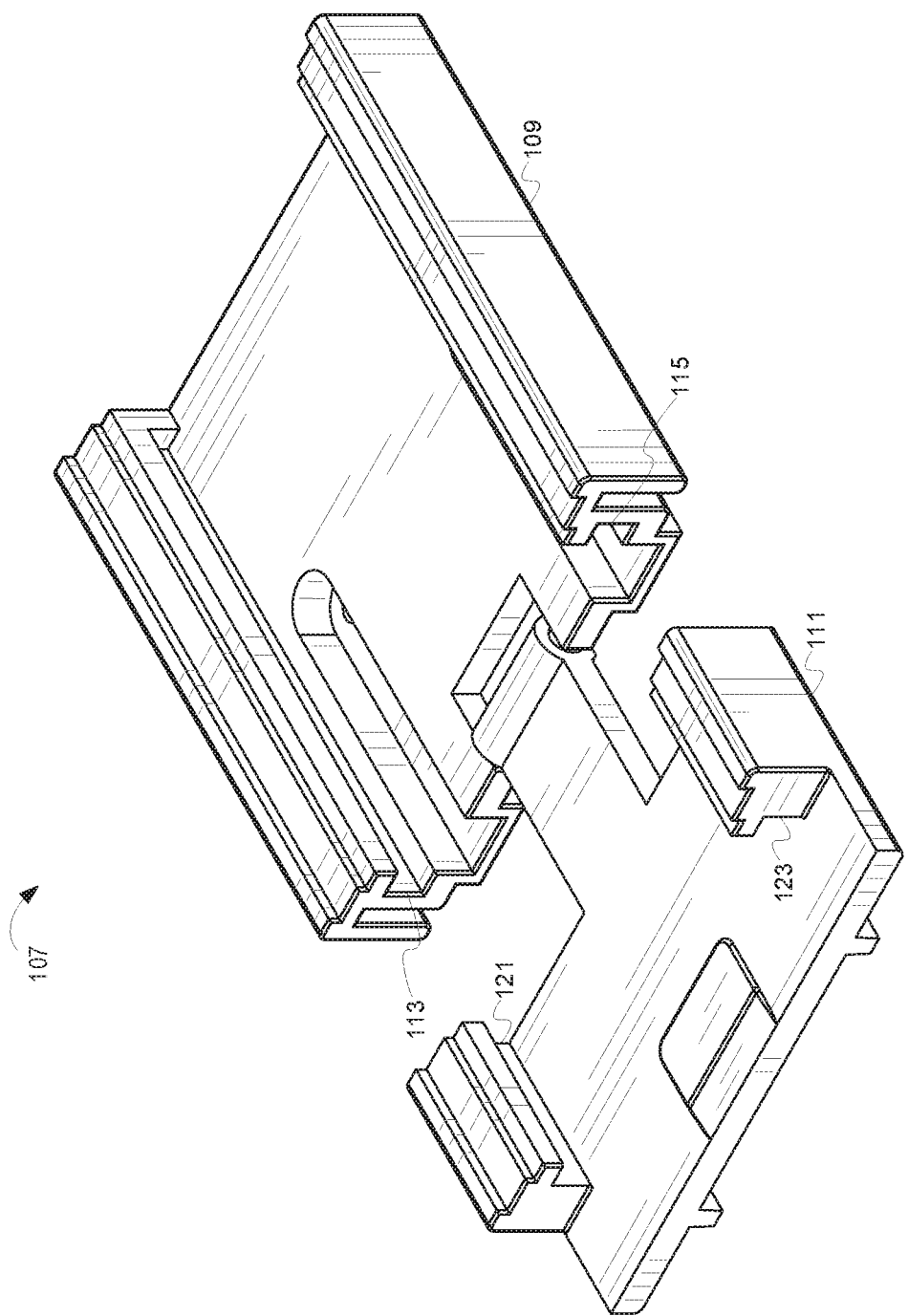
FIG. 7 is a front perspective view of the adapter bracket of the medical device subassembly shown in FIG. 5.
Figure 8:
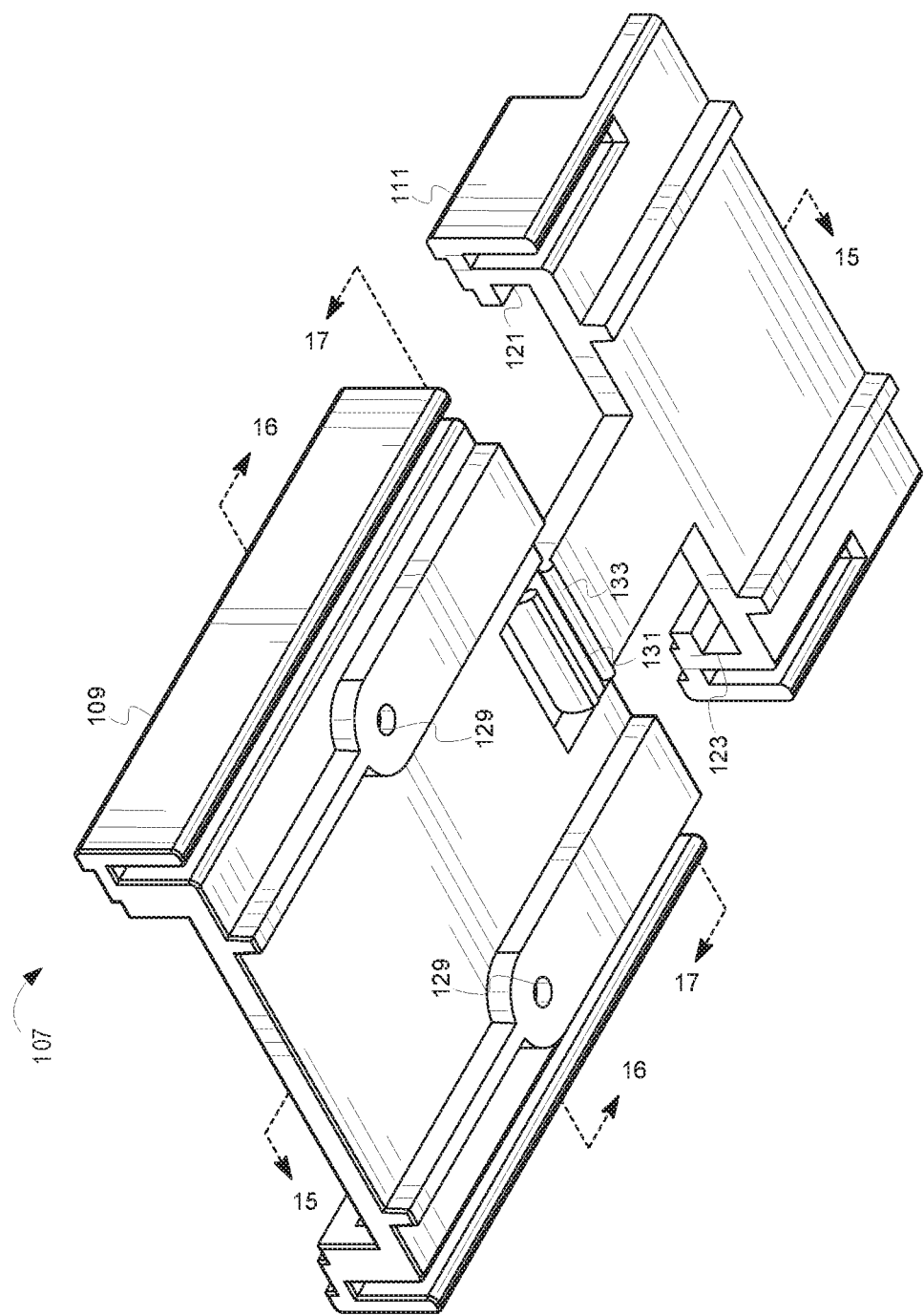
FIG. 8 is a rear perspective view of the adapter bracket shown in FIG. 7.

With particular reference to FIG. 7, the adapter bracket 107 includes a first main body channel 113, a second main body channel 115, a first channel extension 121, and a second channel extension 123. The first main body channel 113 and the second main body channel 115 are disposed on a main body portion 109 of the adapter bracket 107. The first main body channel 113 is located on a first side of the main body portion 109 opposite the second main body channel 115 on a second side of the main body portion 109. The first channel extension 121 and the second channel extension 123 are disposed on a second body portion 111 of the adapter bracket 107. The first channel extension 121 is located on a first side of the second body portion 111 opposite the second channel extension 123 on a second side of the second body portion 111. When the adapter bracket 107 is secured to the wall-mounted bracket 105, the first main body channel 113 and the first channel extension 121 are axially aligned and the second main body channel 115 and the second channel extension 123 are axially aligned (as shown in FIGS. 11 and 12).

Figure 3:
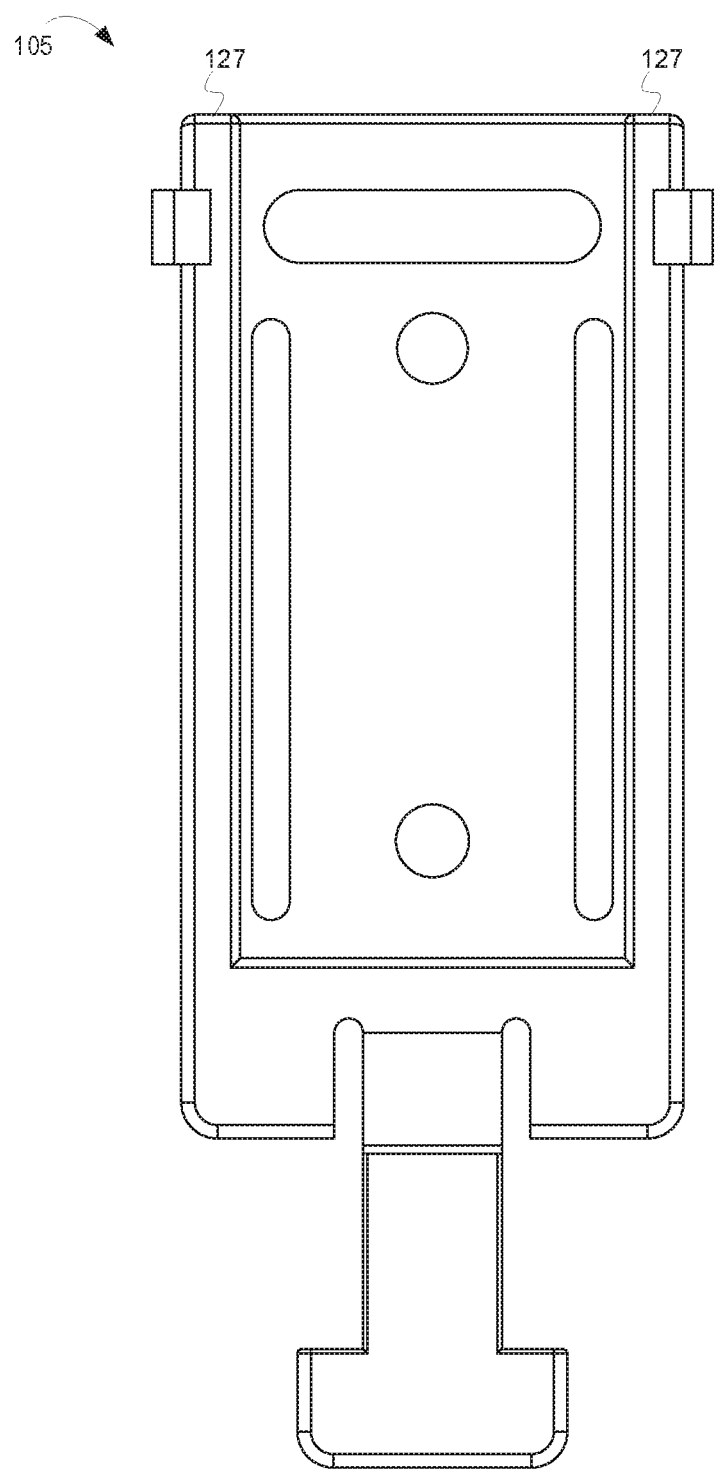
FIG. 3 is a front elevational view of the wall-mounted bracket of the medical device assembly of FIG. 2.
Figure 4:
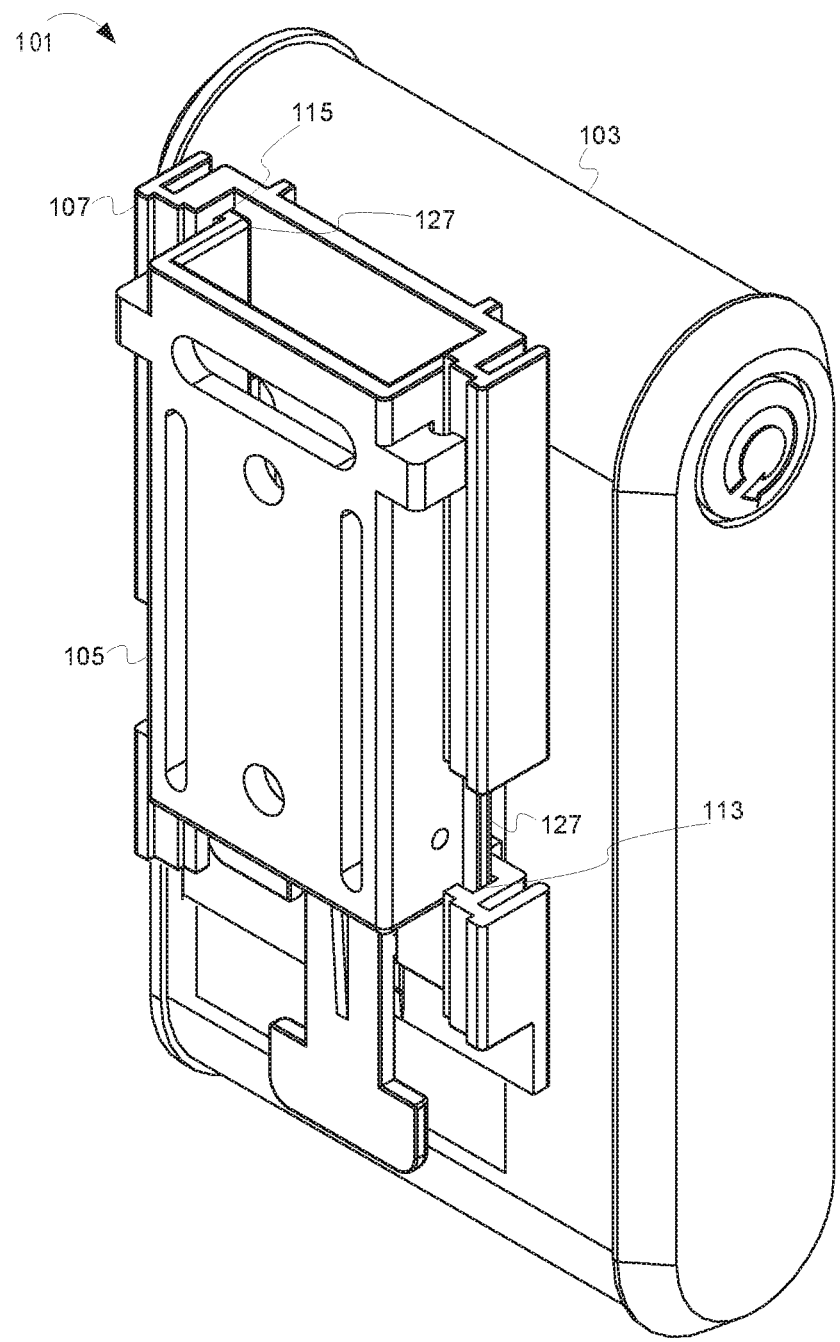
FIG. 4 is a rear perspective view of the wall-mounted medical device assembly shown in FIG. 2.
Figure 5:
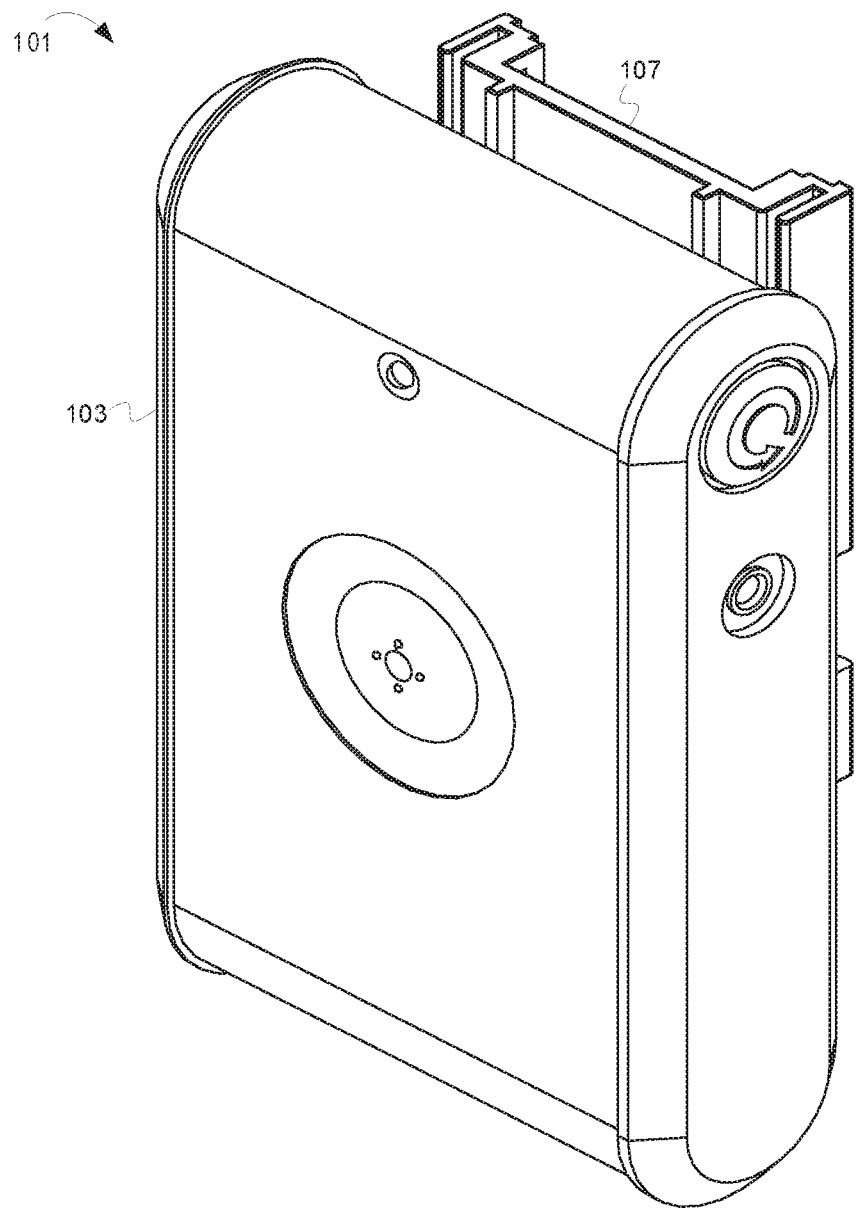
FIG. 5 is a front perspective view of a medical device subassembly that includes medical device secured to the adapter bracket of the medical device assembly shown in FIG. 4.
Figure 6:
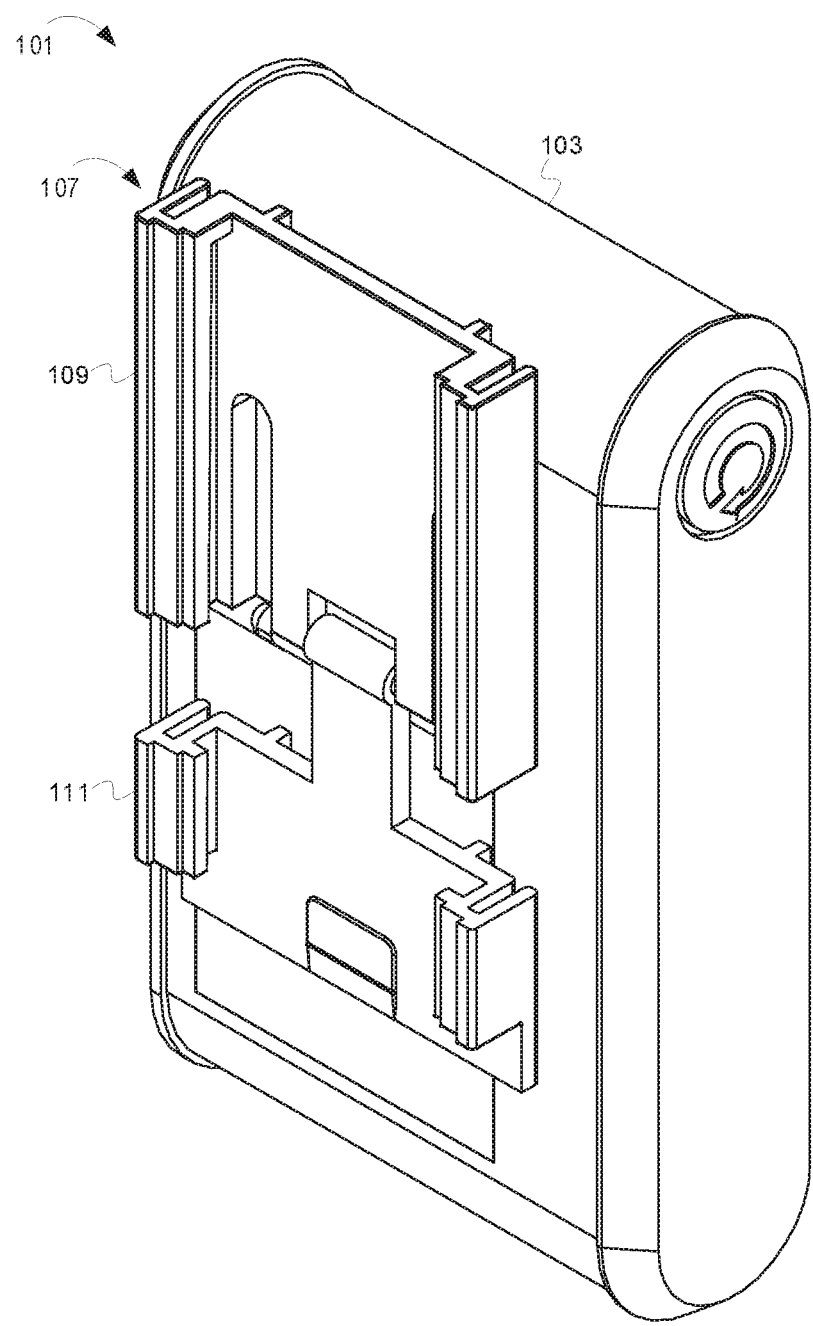
FIG. 6 is a perspective view of the rear portion of the medical device subassembly shown in FIG. 5.

The wall-mounted bracket 105 has a series of rails 127, as seen in FIG. 2 and FIG. 3. The rails 127 engage the channels of the adapter bracket 107. More specifically, the rails 127 of the wall-mounted bracket 105 engage the first main body channel 112, the second main body channel 115, the first channel extension 121, and the second channel extension 123.

Figure 13:
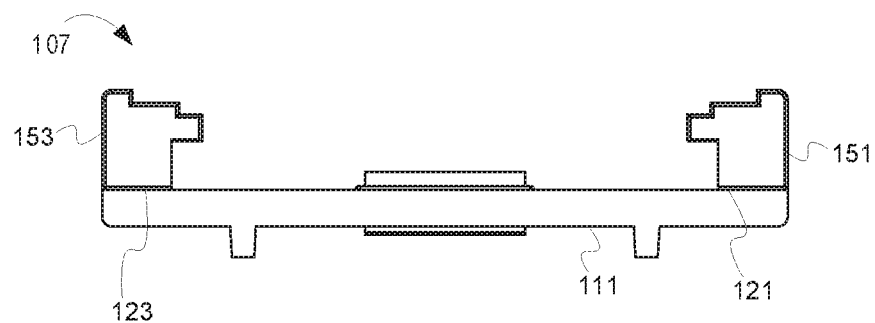
FIGS. 13 and 14 are top plan views of the second body portion and the main body portion, respectively, of the adapter bracket shown in FIG. 7.
Figure 14:
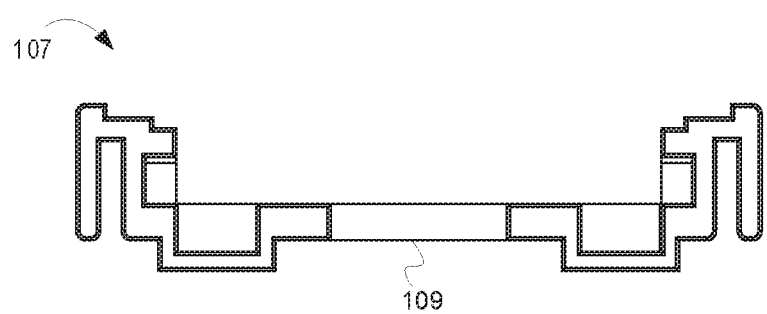
Figure 16:
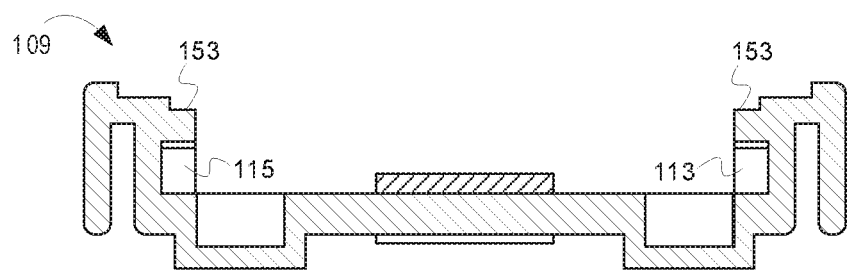
FIG. 16 is a cross-sectional view taken along line 16-16 in FIG. 8.

As seen in FIG. 13, the first channel extension 121 and the second channel extension 123 extend along the length of the second body portion 111. The first channel extension 121 and the second channel extension 123 are formed in the second body portion side members 151. As seen in FIG. 16, the first main body channel 113 and the second main body channel 115 are voids formed by the main body portion side members 153. The rails 127 of the wall-mounted bracket 105 seat in the channels to secure the adapter bracket 107 to the wall-mounted bracket 105.

Figure 17:
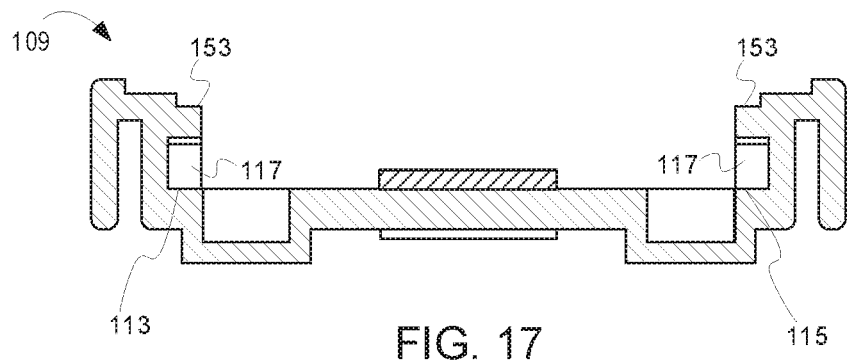
FIG. 17 is a cross-sectional view taken along line 17-17 in FIG. 8.
Figure 18:
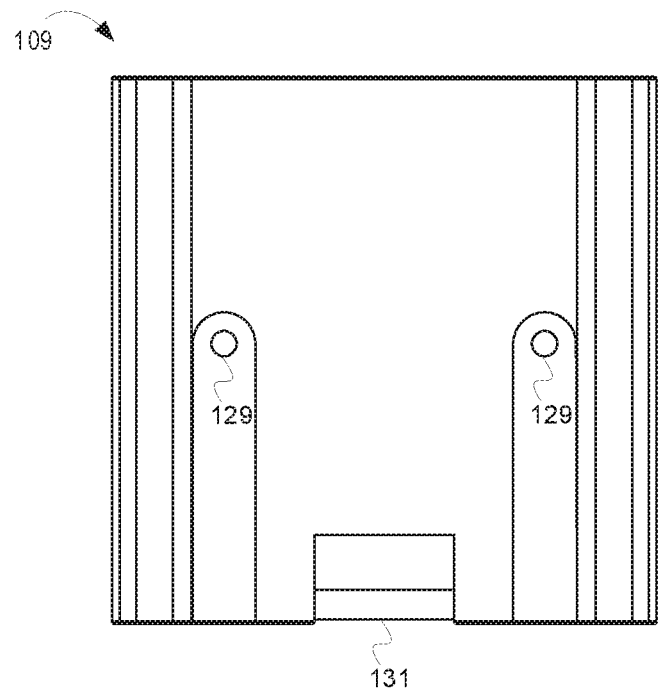
FIG. 18 is a front elevational view of the main body portion of the adapter bracket shown in FIG. 7.
Figure 19:
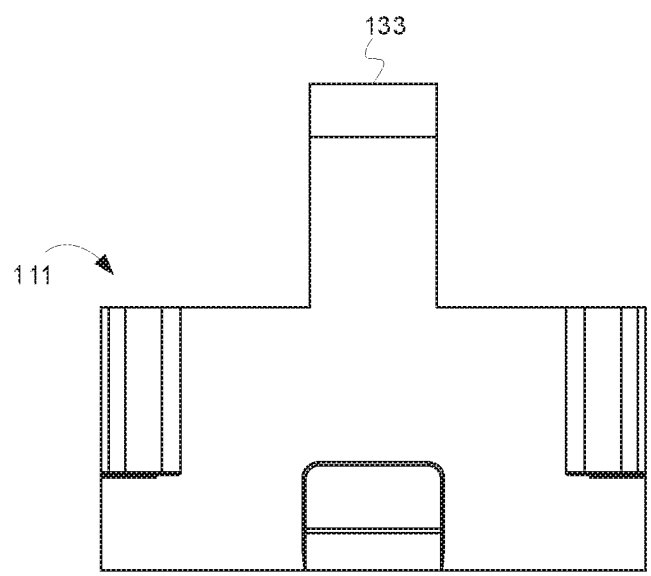
FIG. 19 is a front elevational view of the second body portion of the adapter bracket shown in FIG. 7.
Figure 20:
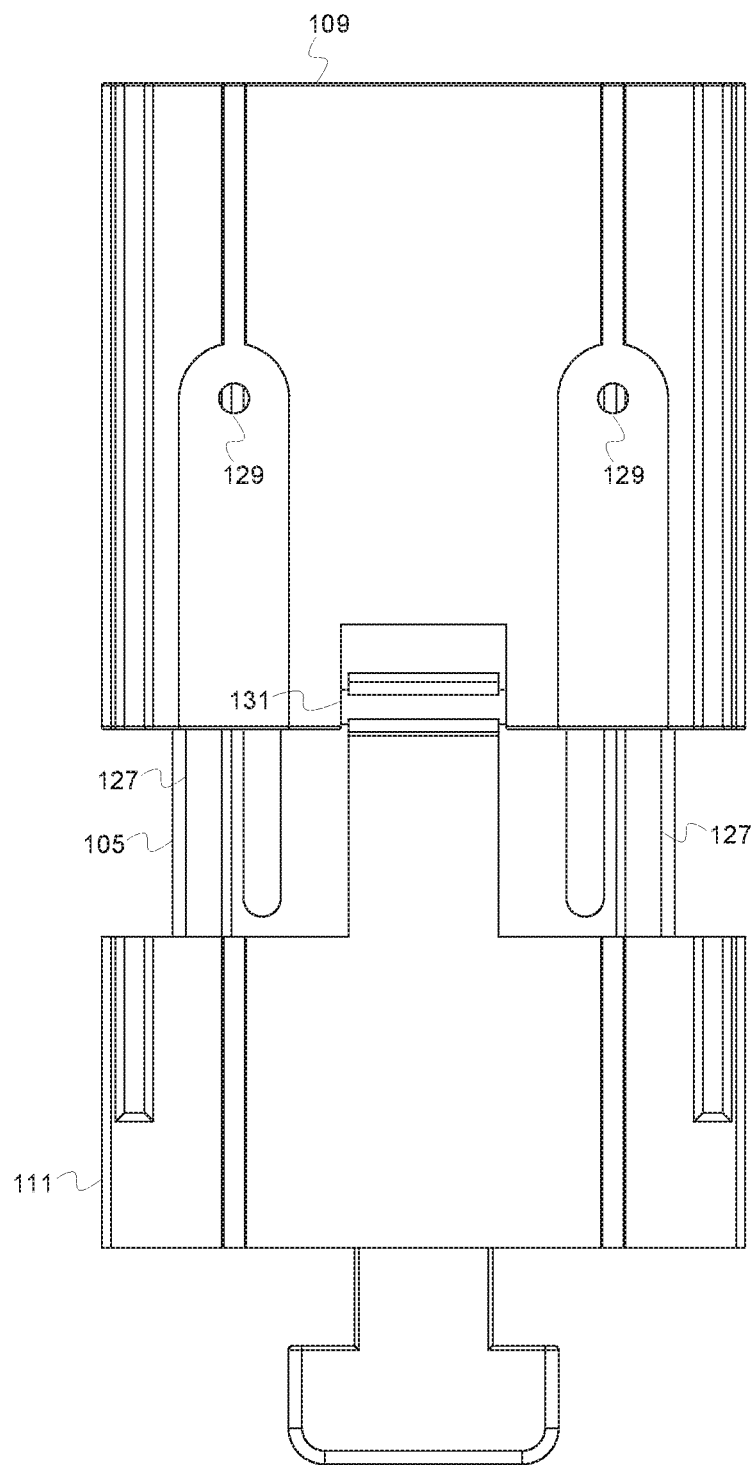
FIG. 20 is a front elevational view of the adapter bracket of FIG. 6 secured to the wall-mounted bracket of FIG. 3, with no medical device depicted.

As seen in FIG. 17, a sectional view of the main body portion 109 viewed toward the top of the main body portion 109, the first main body channel 113 and the second main body channel 115 include position limit stops 117. The position limit stops 117 are located near the top of the first main body channel 113 and the second main body channel 115. The position limit stops 117 limit the extent to which the rails 127 of the wall-mounted bracket 105 can be inserted into the channels of the adapter bracket 107 and thereby support the adapter bracket 107 and thereby the device 103.

Figure 9:
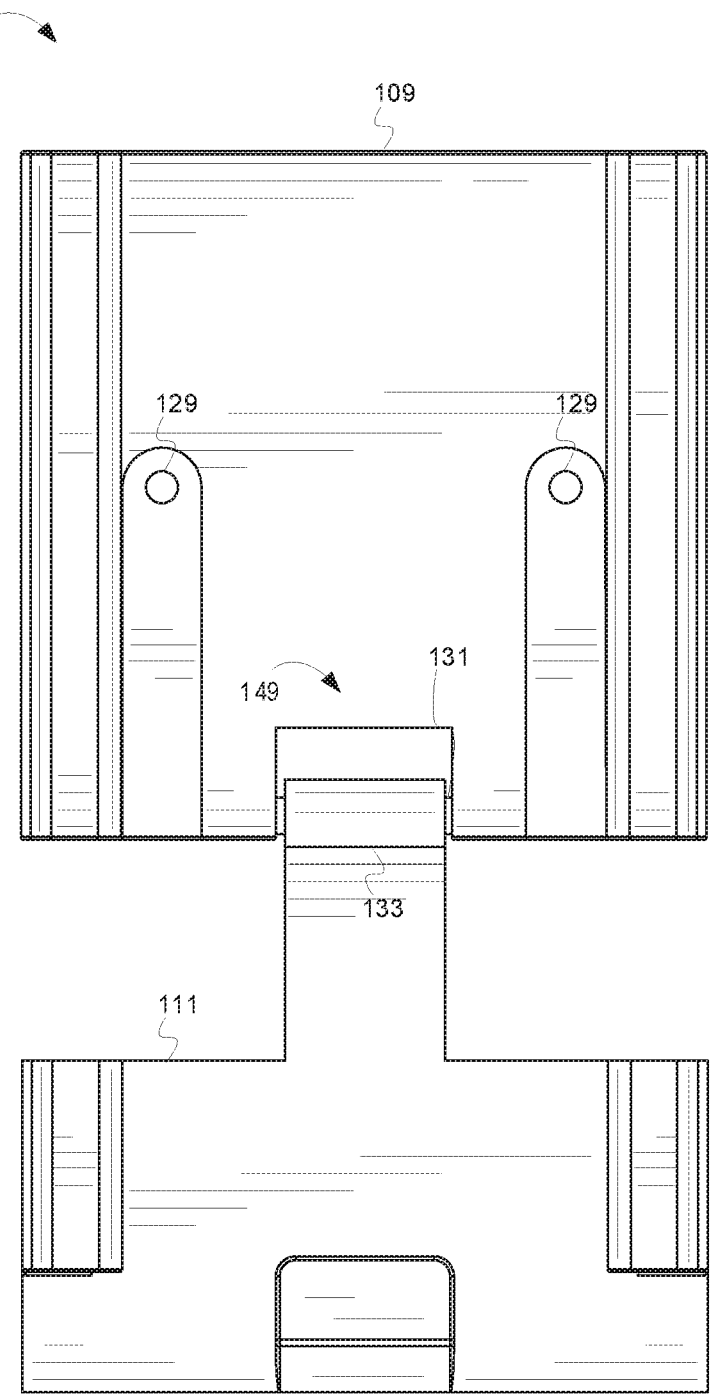
FIG. 9 is a front elevational view of the adapter bracket shown in FIG. 7.
Figure 10:
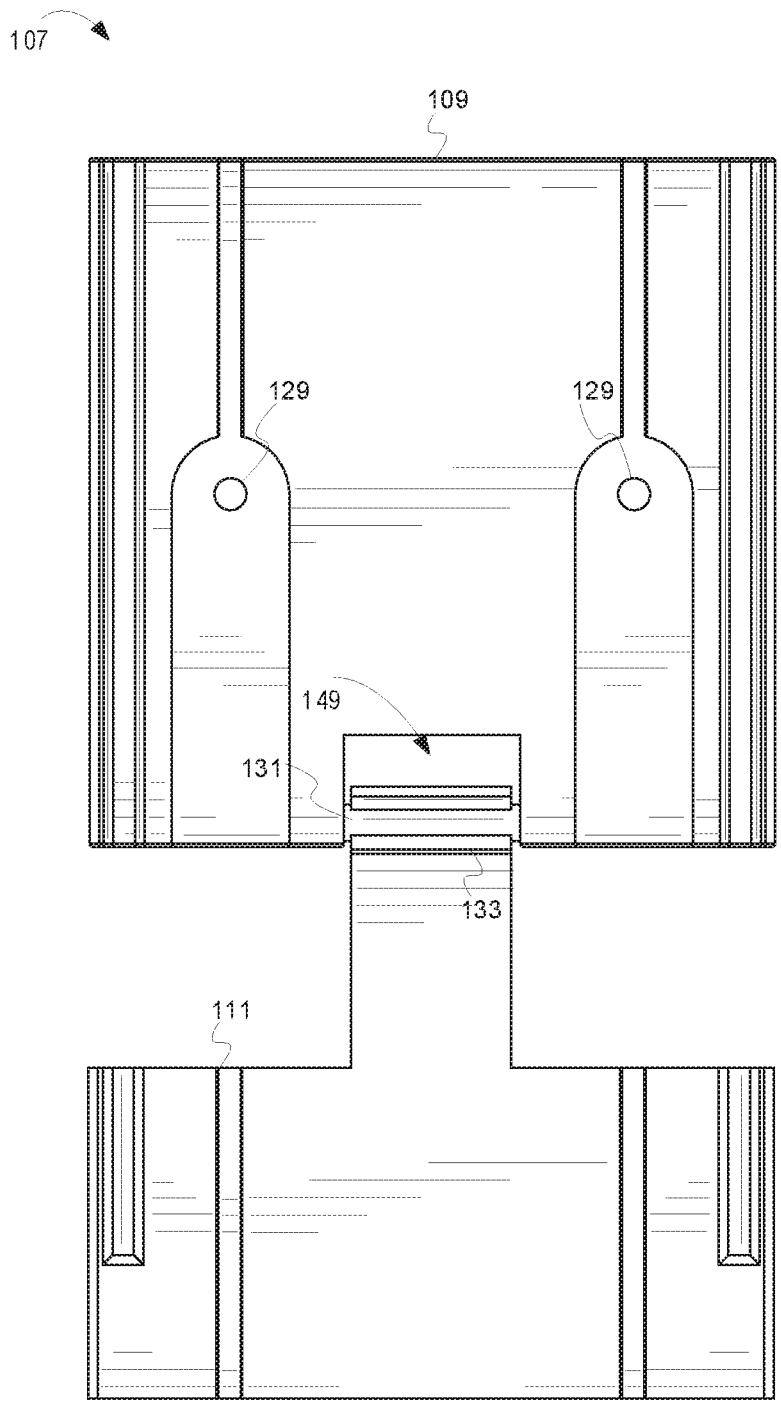
FIG. 10 is a rear elevational view of the adapter bracket shown in FIG. 7.
Figure 15:
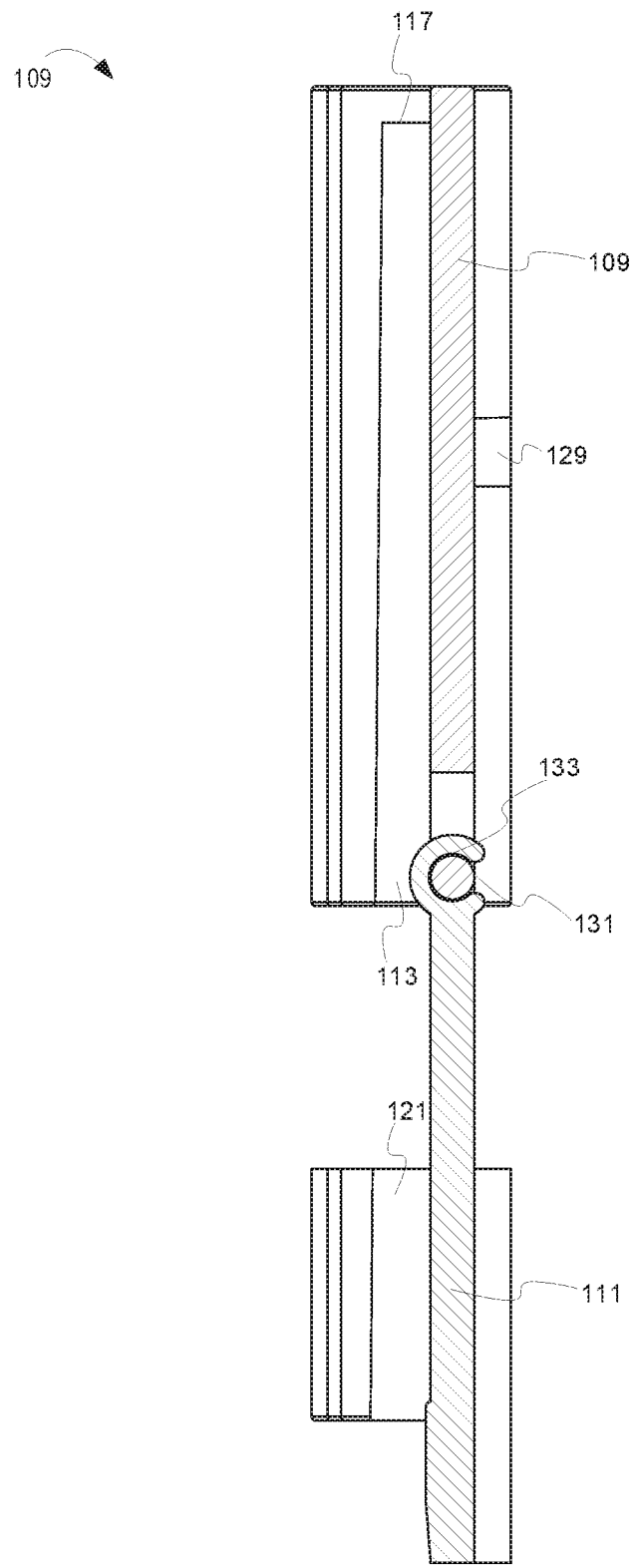
FIG. 15 is a cross-sectional view taken along line 15-15 in FIG. 8.

The main body portion 109 and the second body portion 111 are connected via a hinge 149 (FIG. 15). The hinge can be of any suitable type, such as a living hinge. In the examples shown, the hinge comprises a bar 131 and a curved bearing surface 133. The main body portion 109 includes the bar 131 while the second body portion 111 includes the curved bearing surface 133, although in practice these could be reversed. As seen in FIGS. 9 and 10, the second body portion 111 is secured to the main body portion 109 via the hinge 149. As depicted in the sectional view shown in FIG. 15, the curved bearing surface 133 engages the bar 131 to allow the second body portion 111 to pivot with respect to the main body portion 109.

Figure 21:
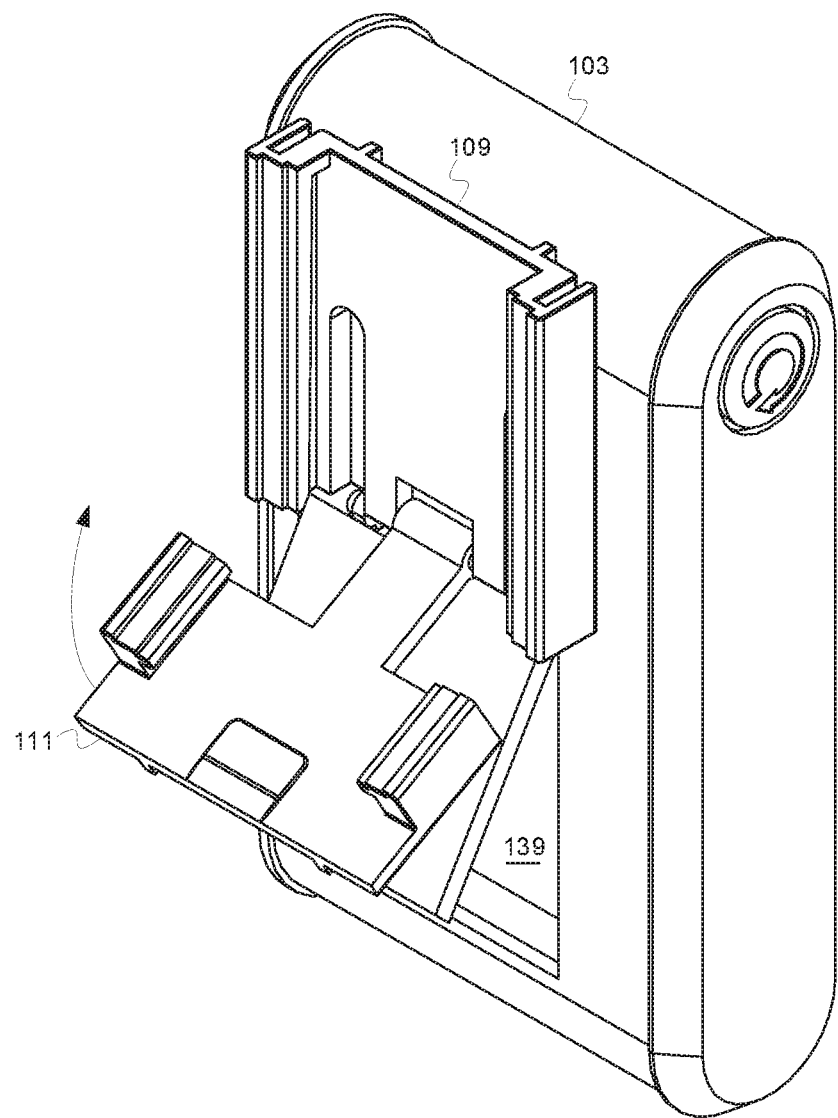
FIG. 21 is a perspective view of the rear portion of medical device subassembly similar to FIG. 6 but depicting the second body portion of the adapter bracket in a pivoted position to allow access to a battery compartment of the medical device.

The hinge 149 allows the second body portion 111 to pivot with respect to the main body portion 109. As seen in FIG. 21, the second body portion 111 is pivoted with respect to the main body portion 109, as indicated by an arrow 137, to allow access to a battery compartment 139 of the medical device 103. In some embodiments, the hinge 149 allows access to the battery compartment 139 without removal of the adapter bracket 107 from the medical device 103. In other embodiments, the second body portion 111 pivots to allow access to a rear control panel of the medical device 103. Though depicted as two separate pieces, in some embodiments, the main body portion 109 and the second body portion 111 can be formed from a single piece. In such embodiments, the hinge 149 may be a living hinge.

As seen in FIGS. 9 and 10, the adapter bracket 107 includes mounting holes 129. The mounting holes 129 are used to secure the adapter bracket 107 to the medical device 103 via, for example, fasteners such as screws.

When using the adapter bracket 107 to secure the medical device 103 to the wall-mounted bracket 105, a user removes the existing medical device, if any, from the wall-mounted bracket, secures the medical device 103 to the adapter bracket 107 via the mounting holes 129, and secures the adapter bracket 107 to the wall-mounted bracket 105 by engaging the rails 127 of the wall-mounted bracket 105 with the channels of the adapter bracket 107.

Figure 22:
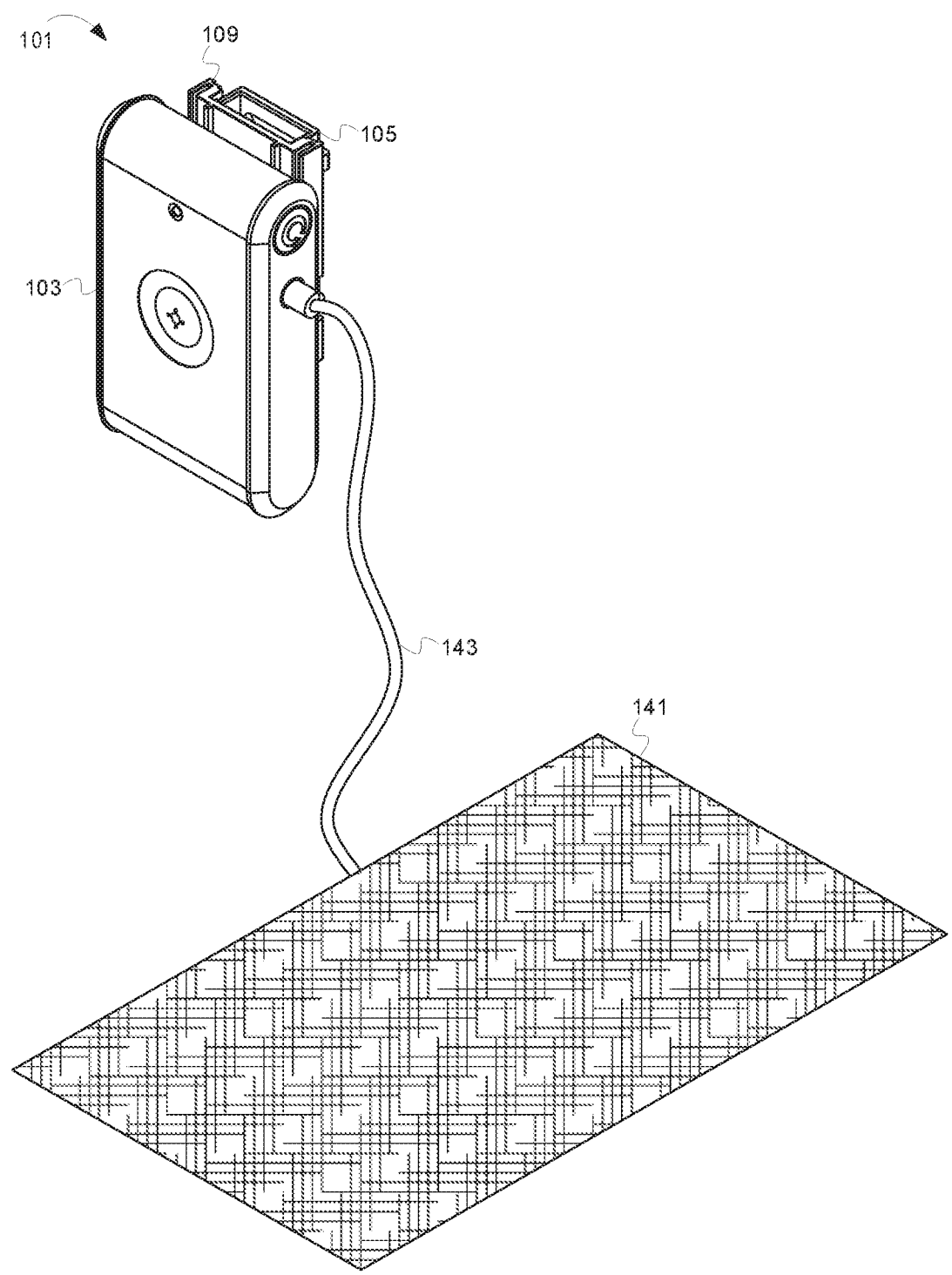
FIG. 22 is a representational view depicting the medical device assembly of FIG. 2 in conjunction with a pressure-sensitive mat for detecting patient falls.

In an exemplary embodiment, the medical device 103 can be a fall alarm for a pressure-sensitive mat 141, as shown in FIG. 22. In such embodiments, the pressure-sensitive mat detects the presence of a patient and the alarm sounds if the patient is no longer detected, signifying that the patient possibly has fallen. The pressure-sensitive mat 141 is communicatively coupled to the medical device 103 via a cable 143.

Figure 23:
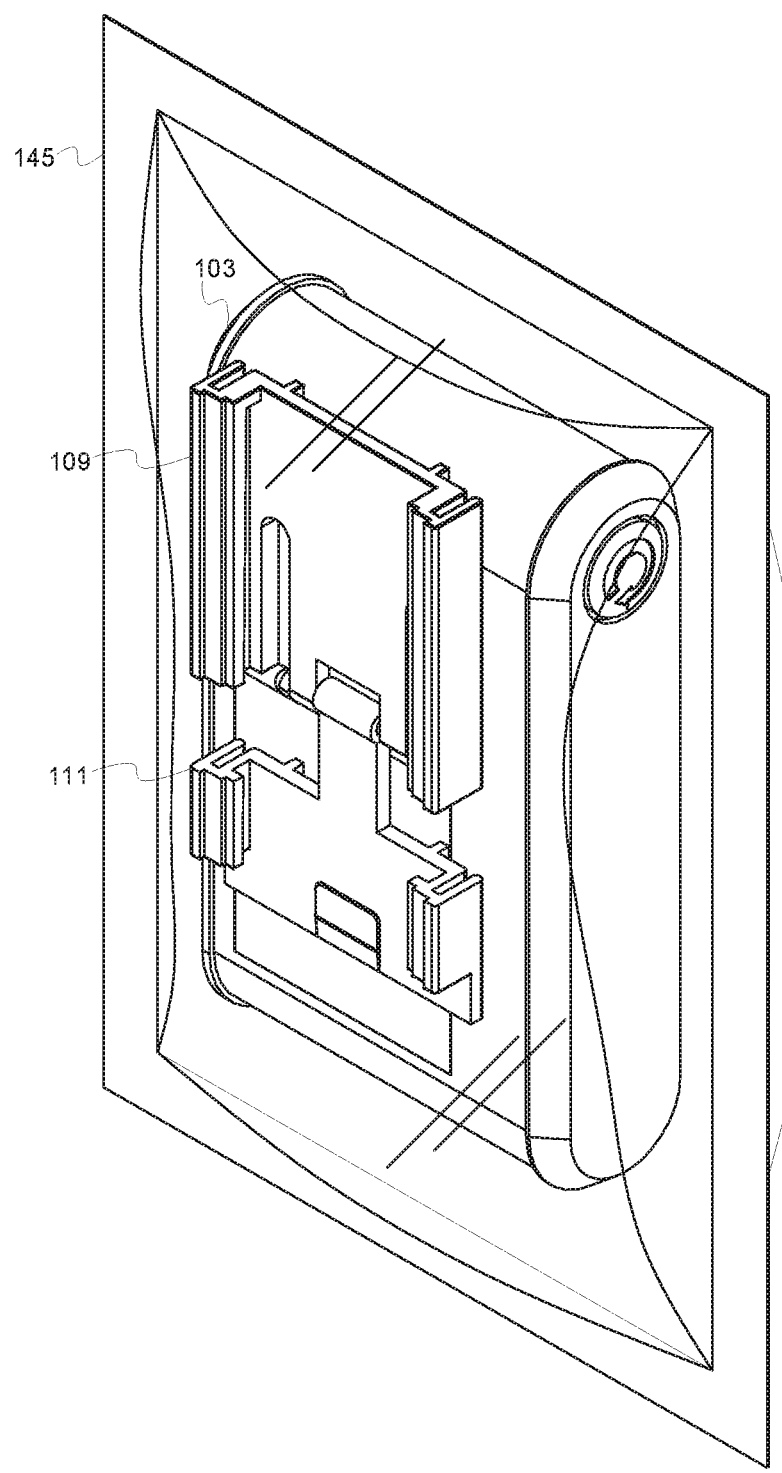
FIG. 23 is a perspective view of a sealed package containing the medical device subassembly of claim 2 and not including a wall-mounted bracket.

In some embodiments, the medical device 103 and the adapter bracket 107 are provided in a sealed package 145, as depicted in FIG. 23. In such embodiments, the medical device 103 and the adapter bracket 107 can be sold as a kit. The kit does not include the wall-mounted bracket 105, although a wall-mounted bracket could optionally be included. In some embodiments, the kit can include multiple adapter brackets. The multiple adapter brackets can be differently sized and/or shaped to accommodate a number of other brackets (e.g., wall-mounted bracket 105 and various other brackets).

All methods described herein can be performed in any suitable order unless otherwise indicated herein or otherwise clearly contradicted by context. The use of any and all examples, or language describing an example (e.g., "such as") provided herein, is intended to illuminate the invention and does not pose a limitation on the scope of the invention. Any statement herein as to the nature or benefits of the invention or of the preferred embodiments is not intended to be limiting. This invention includes all modifications and equivalents of the subject matter recited herein as permitted by applicable law. Moreover, any combination of the above-described elements in all possible variations thereof is encompassed by the invention unless otherwise indicated herein or otherwise clearly contradicted by context. The description herein of any reference or patent, even if identified as "prior," is not intended to constitute a concession that such reference or patent is available as prior art against the present invention. No unclaimed language should be deemed to limit the invention in scope. Any statements or suggestions herein that certain features constitute a component of the claimed invention are not intended to be limiting unless reflected in the appended claims. Neither the marking of the patent number on any product nor the identification of the patent number in connection with any service should be deemed a representation that all embodiments described herein are incorporated into such product or service.

What is claimed is:

1. A medical device subassembly comprising an adapter bracket secured to a battery-powered medical device, the adapter bracket securable to a wall-mounted bracket and comprising:

a main body portion comprising a main body panel, a first main body channel disposed on a first side of the main body panel and a second opposing main body channel disposed on a second side of the main body panel, each of said first and second main body channels including a position limit stop;

a second body portion comprising a second body panel, the second body panel being pivotally connected to the main body panel, the second body panel being pivotable to an aligned position in which a first channel extension is axially aligned with the first main body channel and a second channel extension is axially aligned with the second main body channel, the main body panel being secured to a rear portion of the medical device and the second body panel being positioned adjacent a battery compartment of the medical device and covering said battery compartment when said second body panel is in said aligned position, the second body panel being pivotable to at least one a second position not covering the battery compartment and thereby permitting access to the battery compartment.

2. The medical device subassembly of claim 1, the adapter bracket including a hinge pivotally connecting the main body panel to the second body panel, the hinge including a bar disposed on one of the main body panel and second body panel and a curved bearing surface disposed on the other of the main body panel and second body panel.

3. A sealed package including the medical device subassembly of claim 1 and not including the mating wall-mounted bracket to which the adapter bracket is securable.

4. A medical device subassembly comprising an adapter bracket secured to a battery-powered medical device, the adapter bracket securable to a wall-mounted bracket and comprising:

a main body portion comprising a main body panel, a first main body channel disposed on a first side of the main body panel and a second opposing main body channel disposed on a second side of the main body panel, each of said first and second main body channels including a position limit stop;

a second body portion comprising a second body panel, the second body panel being pivotally connected to the main body panel, the second body panel being pivotable to an aligned position in which a first channel extension is axially aligned with the first main body channel and a second channel extension is axially aligned with the second main body channel, the medical device comprising a fall alarm.

5. A medical device assembly comprising a medical device subassembly comprising an adapter bracket secured to a battery-powered medical device, the medical device subassembly being sized to mate with and secured to a wall-mounted bracket, the adapter bracket comprising a main body portion comprising a main body panel, a first main body channel disposed on a first side of the main body panel and a second opposing main body channel disposed on a second side of the main body panel, each of said first and second main body channels including a position limit stop;

a second body portion comprising a second body panel, the second body panel being pivotally connected to the main body panel, the second body panel being pivotable to an aligned position in which a first channel extension is axially aligned with the first main body channel and a second channel extension is axially aligned with the second main body channel, the wall-mounted bracket comprising a bracket body portion and first and second rails, the first channel extension being aligned with the first main body channel and the second channel extension being aligned with the second main body channels and the first and second rails engaging the first and second main body channels and first and second channel extensions.

6. The medical device assembly of claim 5, the medical device comprising a fall alarm.

7. The medical device assembly of claim 5, the rails engaging the position limit stops.

\* \* \* \* \*

UNITED STATES PATENT AND TRADEMARK OFFICE
CERTIFICATE OF CORRECTION

PATENT NO. : 10,813,476 B2
APPLICATION NO. : 16/289030
DATED : October 27, 2020
INVENTOR(S) : Arun Kousik et al.

Page 1 of 1

It is certified that error appears in the above-identified patent and that said Letters Patent is hereby corrected as shown below:

In Claim 1 (Column 5, Lines 13-14), delete "a" after "at least one", therefor.

Signed and Sealed this
Twenty-second Day of December, 2020

Andrei Iancu
*Director of the United States Patent and Trademark Office*